United States Patent
Pasic et al.

(10) Patent No.: US 6,582,754 B1
(45) Date of Patent: Jun. 24, 2003

(54) COATING PROCESS

(75) Inventors: Paul Pasic, Melbourne (AU); Hans Jörg Griesser, The Patch (AU); Peter Kambouris, Carindale (AU); Peter Chabrecek, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/697,861

(22) Filed: Oct. 27, 2000

(30) Foreign Application Priority Data

Oct. 27, 1999 (EP) .............................. 99810977

(51) Int. Cl.$^7$ .............................. B05D 1/38; A61I 27/00
(52) U.S. Cl. ...................... 427/2.24; 427/2.1; 427/2.31; 427/487; 427/491; 427/301; 427/322; 427/333; 427/407.1
(58) Field of Search .................................. 427/2.1, 2.24, 427/2.31, 487, 491, 301, 322, 333, 407.1

(56) References Cited

U.S. PATENT DOCUMENTS 6,169,127 B1 * 1/2001 Lohmann et al. ............ 523/106
6,200,626 B1 * 3/2001 Grobe, III et al. ........ 427/20.24

FOREIGN PATENT DOCUMENTS

| EP | 0 484 886 B1 | 11/1991 |
| GB | 2054615 A | 6/1989 |
| JP | 01091428 | 11/1989 |
| WO | WO 94/06485 | 3/1994 |

OTHER PUBLICATIONS

European Search Report.

* cited by examiner

Primary Examiner—Shrive P. Beck
Assistant Examiner—Jennifer Kolb Michener
(74) Attorney, Agent, or Firm—Jian S. Zhou; Richard I. Gearhart; R. Scott Meece

(57) ABSTRACT

The invention relates to a process for coating a material surface, comprising the steps of:

(a) covalently binding a compound comprising an ethylenically unsaturated double bond to the material surface;

(b) polymerizing a monomer comprising a reactive or crosslinkable group on the surface and thereby providing a primary polymer coating comprising reactive or crosslinkable groups, (c) in case of a monomer comprising a reactive group in step (b) reacting the reactive groups of the primary coating with a further compound comprising an ethylenically unsaturated double bond and graft-polymerizing a hydrophilic monomer and optionally a co-monomer having a crosslinkable group onto the primary coating obtained according to step (b) and (d) in case of crosslinkable groups being present in step (b) or (c) initiating crosslinking of said groups. The coated articles that are obtainable by the process of the invention have desirable characteristics regarding adherence to the substrate, durability, hydrophilicity, wettability, biocompatibility and permeability and are thus useful for the manufacture of biomedical articles such as ophthalmic devices.

13 Claims, No Drawings

COATING PROCESS

The present invention is directed to a process for the manufacture of branched and optionally crosslinked coatings on bulk polymeric materials with high wettability by aqueous biological media and minimal irreversible adsorption of proteins, and their use for biomedical applications, especially contact lenses including extended-wear contact lenses. The need for highly wettable, minimally protein-fouling coatings is well recognized particularly in the contact lens field. Bulk polymeric materials that possess high oxygen permeability are of great interest for application as extended wear contact lenses. Unfortunately polymers that provide high oxygen transmission possess a relatively hydrophobic surface even if their water content is in the range of 20 to 30%. This leads to excessive discomfort and unacceptably rapid dewetting of the lens by the tear film when such lenses are worn by humans. Hence such contact lens bulk materials must be equipped with a coating that allows good wetting by the human tear fluid. Application of thin polymeric coatings, for instance from gas plasmas (glow discharges) struck in methane/air mixtures ameliorates this problem and enables comfortable wear of such composite lenses. However, the irreversible deposition of biological molecules (biofouling), particularly proteins, onto such coated lenses can lead to the onset of symptoms of discomfort in some wearers and therefore still presents a drawback that needs to be overcome to obtain an ultimately comfortable lens for even the most sensitive wearers.

It is the object of the present invention to provide hydrophilic polymer coatings that have the desirable property of providing superior resistance to fouling of contact lenses by tear film proteins while also allowing high wettability by the tear film. Surprisingly, this can be achieved by the use of branched and optionally crosslinked hydrophilic polymer-containing chains. The coatings of the present invention have been found to result in no observable protein adsorption even when complex multi-protein solutions were used, such as human tear fluid. Exposure to multicomponent protein media presents a far more demanding challenge for coatings intended to be protein-resistant than exposure to single protein solutions, and hence the protein-resisting abilities of the coatings of the present invention are clearly demonstrated.

The present invention therefore in one aspect relates to a process for coating a material surface, comprising the steps of: Coating Process
  (a) covalently binding a compound comprising an ethylenically unsaturated double bond to the material surface;
  (b) polymerizing a monomer comprising a reactive or crosslinkable group on the surface and thereby providing a primary polymer coating comprising reactive or crosslinkable groups,
  (c) in case of a monomer comprising a reactive group in step (b) reacting the reactive groups of the primary coating with a further compound comprising an ethylenically unsaturated double bond and graft-polymerizing a hydrophilic monomer and optionally a co-monomer having a crosslinkable group onto the primary coating obtained according to step (b) and
  (d) in case of crosslinkable groups being present in step (b) or (c) initiating crosslinking of said groups.

Examples of materials that may be coated according to the process of the invention are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); elastomers (silicones, polybutadiene and polyisoprene); or modified or unmodified biopolymers (collagen, cellulose, chitosan and the like).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoropolyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of materials to be coated are those being conventionally used for the manufacture of biomedical devices, e.g. contact lenses, which are hydrophilic per se, since reactive groups, e.g. carboxy, carbamoyl, sulfate, sulfonate, phosphate, amine, ammonium or hydroxy groups, are inherently present in the material and therefore also at the surface of a biomedical device manufactured therefrom. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol or copolymers for example from two or more monomers from the group hydroxyethyl acrylate, hydroxyethyl methacrylate, N-vinyl pyrrolidone, acrylic acid, methacrylic acid, acrylamide, dimethyl acrylamide, vinyl alcohol and the like. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

Still another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740 which are herewith incorporated by reference.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or a composite made therefrom.

Moreover, the material to be coated may also be an inorganic or metallic base material with or without suitable reactive groups, e.g. ceramic, quartz, or metals, such as silicon or gold, or other polymeric or non-polymeric substrates. E.g. for implantable biomedical applications, ceramics or carbohydrate containing materials such as polysaccharides are very useful. In addition, e.g. for biosensor purposes, dextran coated base materials are expected to reduce nonspecific binding effects if the structure of the coating is well controlled. Biosensors may require polysaccharides on gold, quartz, or other non-polymeric substrates. The form of the material to be coated may vary within wide limits. Examples are particles, granules, capsules, fibres, tubes, films or membranes, preferably moldings of all kinds such as ophthalmic moldings, in particular contact lenses.

According to step (a) the compound comprising an ethylenically unsaturated group is suitably covalently bound to the surface of the material to be modified on its surface via reaction of a functional group of the material surface with a co-reactive group of the ethylenically unsaturated compound. Suitable functional groups may be inherently (a priori) present at the surface of the material to be modified on its surface. If substrates contain too few or no reactive groups, the material surface can be modified by methods known per se, for example plasma chemical methods (see, for example, WO 94/06485), or conventional functionalization with groups such as —OH, —NH$_2$ or —CO$_2$H. Suitable functional groups may be selected from a wide variety of groups well known to the skilled artisan. Typical examples are e.g. hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. Amino groups and hydroxy groups are preferred.

The compound comprising an ethylenically unsaturated group according to step (a) may be for example, a vinyl monomer having from 2 to 18 C-atoms and preferably from 2 to 10 C-atoms, which is substituted by a reactive group wherein the above-mentioned meanings and preferences apply.

Suitable reactive groups of the vinyl monomer according to step (a) may be a hydroxy, amino, carboxy, carboxylic acid ester, carboxylic acid anhydride, epoxy, lactone, azlactone or isocyanato group. One group of preferred reactive groups comprises carboxy, carboxylic acid anhydride, azlactone or isocyanato, in particular isocyanato. Another group of preferred reactive groups comprises amino or in particular hydroxy.

Suitable vinyl monomers having a reactive group may be compounds of formula

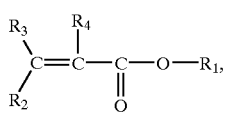

(1a)

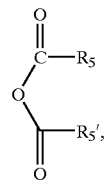

(1b)

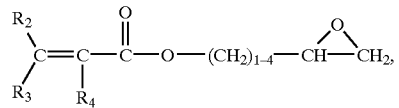

(1c)

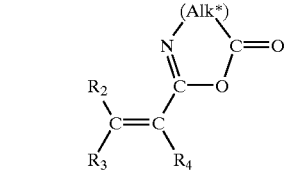

(1d)

or

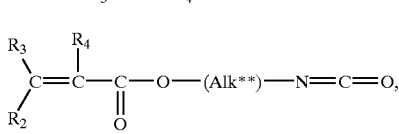

(1e)

wherein R$_1$ is hydrogen, unsubstituted or hydroxy-substituted C$_1$–C$_6$-alkyl or phenyl, R$_2$ and R$_3$ are each independently of the other hydrogen, C$_1$–C$_4$-alkyl, phenyl, carboxy or halogen, R$_4$ is hydrogen, C$_1$–C$_4$-alkyl or halogen, R$_5$ and R$_5$' are each an ethylenically unsaturated radical having from 2 to 6 C-atoms, or R$_5$ and R$_5$' together form a bivalent radical —C(R$_2$)=C(R$_4$)—, and (Alk*) is C$_1$–C$_6$-alkylene, and (Alk**) is C$_2$–C$_{12}$-alkylene.

The following preferences apply to the variables contained in formulae (1a)–(1e):

R$_1$ is preferably hydrogen or hydroxy-C$_1$–C$_4$-alkyl, in particular hydrogen or β-hydroxyethyl.

One of the variables R$_2$ and R$_3$ is preferably hydrogen and the other one is hydrogen, methyl or carboxy. Most preferably R$_2$ and R$_3$ are each hydrogen.

R$_4$ is preferably hydrogen or methyl.

R$_5$ and R$_5$' are preferably each vinyl or 1-methylvinyl, or R$_5$ and R$_5$' together form a radical-C(R$_2$)=C(R$_4$)— wherein R$_2$ and R$_4$ are each independently hydrogen or methyl. (Alk*) is preferably methylene, ethylene or 1,1-dimethyl-methylene, in particular a radical —CH$_2$— or —C(CH$_3$)$_2$—.

(Alk**) is preferably C$_2$–C$_4$-alkylene and in particular 1,2-ethylene.

Particularly preferred vinyl monomers having a reactive group are 2-isocyanatoethylmeth-acrylate (IEM), 2-vinyl-azlactone, 2-vinyl-4,4-dimethyl-azlactone, acrylic acid, methacrylic acid, acrylic acid anhydride, maleinic acid anhydride, 2-hydroxyethylacrylate (HEA), 2-hydroxymethacrylate (HEMA), glycidylacrylate or glycidylmethacrylate.

Throughout the application terms such as carboxy, carboxylic acid, —COOH, sulfo, —SO$_3$H, amino, —NH$_2$ and the like always include the free acid or amine as well as a suitable salt thereof, for example a biomedically or in particular occularly acceptable salt thereof such as, for example, a sodium, potassium, ammonium salt or the like (of an acid), or a hydrohalide such a hydrochloride (of an amine).

In a preferred embodiment of the invention, the covalent bonding between the inorganic or preferably material surface and the compound comprising an ethylenically unsaturated group occurs via reaction of a hydroxy, amino, alkylamino, thiol or carboxy group, particularly of a hydroxy or amino group, of the substrate surface with an isocyanato, azlactone, epoxy, carboxy anhydride, carboxy or hydroxy group, particularly with an isocyanato group, of the ethylenically unsaturated compound, for example using an ethylenically unsaturated compound of formula (1a)–(1e). Suitable methods for this are known from textbooks of organic chemistry. The reaction may be carried out, for example, at elevated temperature, for example from 0° to 100° C. and preferably at room temperature, and optionally in the presence of a catalyst. After the reaction, excess compounds can be removed, for example, with solvents.

According to a preferred embodiment of the invention the material to be coated is an organic polymer containing H-active groups, in particular —OH, —NH$_2$ and/or —NH—, on the surface that are co-reactive with isocyanato groups, some or all of whose H atoms have been substituted by radicals of the formula—C(O)N(H)-(Alk)-OC(O)-C(R$_4$)=CR$_2$(R$_3$), wherein (Alk), R$_2$, R$_3$ and R$_4$ have the meaning given above, particularly 2-isocyanatoethylmethacrylate (IEM).

In step (b) the vinyl monomer having a reactive or crosslinking group may be grafted as such or in admixture with a suitable vinyl co-monomer, preferably a hydrophilic vinyl co-monomer, onto the material surface.

A preferred embodiment of step (b) of the invention concerns co-polymerizing a vinyl monomer comprising a reactive group with a hydrophilic vinyl co-monomer.

Another preferred embodiment of step (b) is the co-polymerization of a vinyl monomer comprising a crosslinkable group, with a hydrophilic vinyl co-monomer.

A suitable vinyl monomer having a reactive group in step (b) independently may be one of the compounds comprising an ethylenically unsaturated group mentioned in step (a) where the above given meanings and preferences apply. A particularly preferred monomer having a reactive group in step (b) is acrylic acid.

Suitable monomers having a crosslinkable group include, without the following being an exhaustive list, difunctionalized active esters, such as ethylene glycolbis [sulfosuccinimidyl-succinate] and bis[sulfosuccinimdyl] suberate, sulfosuccinimidyl[4-azidosalicylamido]hexanoate, difunctional isocyanates, diacrylates such as 1,4-butanedioldiacrylate or α,ω-PEG-diacrylate and diepoxides such as ethyleneglycoldiglycidylether.

Preferably, the crosslinkable monomer is a monofunctonal vinyl monomer, for example a vinyl monomer comprising an isocyanato, epoxy, hydroxy, amino or carboxy functionality. The crosslinking according to step (d) then may be accomplished through these groups, either by reaction with each other or with other functional groups being present in the polymer. For example, when using a monomer having a hydroxyalkyl group such as N-hydroxymethyl acrylamide, the hydroxyalkyl groups of the resulting polymer may be crosslinked afterwards in an acidic medium. Alternatively, functional groups in the resulting polymer such as those mentioned above may be crosslinked afterwards by adding a co-reactive difunctional compound, for example a diamine such as ethylenediamine, a diol, a polyol or a diisocyanate.

The expression "hydrophilic vinyl co-monomer" is understood to mean a monomer that typically produces as homopolymer a polymer that is water-soluble or capable of absorbing at least 10% by weight water.

The proportion of vinyl monomers having a reactive group, if used, is preferably from 0.001 to 1 units per unit of hydrophilic vinyl co-monomer, especially from 0.01 to 0.5 units, more preferably from 0.02 to 0.2 units and in particular from 0.02 to 0.1 units. The number of crosslinking monomers, if used, is preferably from 0.001 to 0.1 units per unit of hydrophilic vinyl co-monomer, especially from 0.01 to 0.05 units and most preferably from 0.01 to 0.02 units.

Suitable hydrophilic vinyl co-monomers include, without the following being an exhaustive list, hydroxy-substituted C$_1$–C$_2$-alkyl acrylates and methacrylates, acrylamide, methacryl-amide, N-mono- or N,N-di-C$_1$–C$_2$-alkylacrylamide and -methacrylamide, ethoxylated acrylates and methacrylates, hydroxy-substituted C$_1$–C$_2$-alkyl vinyl ethers, sodium ethylenesulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino-(the term "amino" also including quaternary ammonium), mono-C$_1$–C$_2$-alkylamino- or di-C$_1$–C$_2$-alkylamino-C$_1$–C$_2$-alkyl acrylates and methacrylates, allyl alcohol and the like. Preferred are acrylamide, N,N-di-C$_1$–C$_2$-alkyl(meth) acrylamides such as N,N-dimethyl acrylamide or five- to seven-membered N-vinyl lactams such as N-vinylpyrrolidone, in particular acrylamide.

The vinyl monomer having a reactive or crosslinking group, optionally in admixture with a hydrophilic vinyl co-monomer, may be applied to the modified material surface and polymerized there according to processes known per se. For example, the material is immersed in a solution of the vinyl monomer(s), or a layer of vinyl monomer(s) is first of all deposited on the modified material surface, for example, by dipping, spraying, spreading, knife coating, pouring, rolling, spin coating or vacuum vapor deposition. Suitable solvents, if used in the polymerization process, are water and, for example, dipolar aprotic solvents such as, for example, acetonitrile. The polymerization of the vinyl monomer(s) on the material surface then may be initiated, for example, thermally by the action of heat or by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend, for example, on the desired properties of the resulting composite material but is usually in the range of up to 30 minutes, preferably from 10 seconds to 10 minutes, and particularly preferably from 0.5 to 5 minutes. It is advantageous to carry out the irradiation in an atmosphere of inert gas. After the polymerization, any non-covalently bonded monomers, oligomers or polymers formed can be removed, for example by treatment with suitable solvents.

In case of a thermally initiated polymerization of the vinyl monomer(s) on the material surface said polymerization may be carried out, for example, at elevated temperature, for example at a temperature of from 35 to 100° C. and preferably 40 to 80° C., for a time period of, for example, from 10 minutes to 48 hours and preferably 30 minutes to 36 hours in the absence or presence of one of the above-mentioned solvents. It is advantageous to carry out the thermally initiated polymerization in an atmosphere of inert gas.

Polymerization initiators are typically those that are initiating a radical polymerization of ethylenically unsaturated compounds. Suitable thermal polymerization initiators are known to the skilled artisan and comprise for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile), 1,1'-azo-bis (1-cyclohexanecarbonitrile), 2,2'-azo-bis(2,4-dimethylvaleronitrile), 4,4'-azo-bis(4-cyanovaleric acid and the like.

Initiators for the radiation-induced polymerization may belong to different types, for example to the thioxanthone type and to the benzoin type, particularly benzoinmethylether, 1-hydroxycyclohexylphenyl ketone, Darocure 1173 and Irgacure types.

By means of the polymerization step (b), the vinyl monomer(s) may be grafted to the bulk material surface with formation of a primary coating comprising a plurality of polymer chains bonded to the surface. Each polymer chain contains reactive groups or crosslinking groups at regular intervals (if the vinyl monomer comprising the reactive or crosslinking group is used without a vinyl co-monomer) or statistically distributed (if the vinyl monomer comprising the reactive or crosslinking group is used in combination with a vinyl co-monomer). The reactive groups that are present in the polymer chains are those mentioned before in the description of the vinyl monomers comprising a reactive group.

A suitable further compound comprising an ethylenically unsaturated double bond in step (c) independently may be one of the compounds comprising an ethylenically unsaturated group mentioned in step (a) where the above given meanings and preferences apply. A particularly preferred compound having an ethylenically unsaturated double bond in step (c) is IEM.

A suitable hydrophilic monomer used in step (c) may be one of the hydrophilic vinyl co-monomers mentioned in step (b), wherein the above given meanings and preferences apply.

A suitable crosslinking monomer used in step (c) may be one of the monomers having a crosslinkable group as mentioned in step (b) wherein the above given meanings and preferences apply.

A preferred embodiment of step (c) comprises first of all reacting a compound comprising an ethylenically unsaturated double bond, in particular IEM, with the primary coating obtained according to step (b) and then graft polymerizing a hydrophilic monomer, in particular acrylamide, onto the primary coating.

A further preferred embodiment of step (c) comprises first of all reacting a compound comprising an ethylenically unsaturated double bond, in particular IEM, with the primary coating obtained according to step (b) and then graft polymerizing a mixture of a hydrophilic monomer, in particular acrylamide, and a crosslinking monomer onto the primary coating.

The graft polymerization in step (c) may be accomplished as described in step (b).

One embodiment of the optional step (d) comprises the crosslinking of crosslinkable groups being present on the modified material surface after step (b) or (c) with a difunctional compound selected from the group consisting of diisocyanates, diamines, dioles, 1,4-butanedioldiacrylates and α,ωPEG-diacrylates. A further embodiment of the optional step (d) comprises the crosslinking of crosslinkable groups being present on the modified material surface after step (b) or (c) by means of an addition or condensation reaction.

The coated material obtained according to the invention may be purified afterwards in a manner known per se, for example by washing or extraction with a suitable solvent such as water.

The coating thickness of the coated material surfaces obtained according to the process of the invention depends principally on the desired properties. It can be, for example, from 0.001 to 1000 $\mu$m, preferably from 0.01 to 500 $\mu$m, more preferably from 0.01 to 100 $\mu$m, even more preferably from 0.05 to 50 $\mu$m, especially preferably from 0.1 to 5 $\mu$m and particularly preferably from 0.1 to 1 $\mu$m.

A further embodiment of the invention relates to a material that is coated by the process of the invention.

The material that is coated by the process of the invention is, for example, an organic bulk material, preferably a biomedical device, e.g. an ophthalmic device, preferably a contact lens including both hard and particularly soft contact lenses, an intraocular lens or artificial cornea. Further examples are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices, e.g. ophthalmic devices obtained according to the invention have a variety of unexpected advantages over those of the prior art which make those devices very suitable for practical purposes,e.g. as contact lens for extended wear or intraocular lens.

For example, they do have a high surface wettability which can be demonstrated by their contact angles, their water retention and their water-film break up time or tear film break up time (TBUT).

The TBUT plays an particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, Focus Dailies ™, Focus New Vuess or Lotrafilcon A lenses, by applying a surface coating according to the invention. On the base curve of a contact lens, the pronounced lubricity of the coating facilitates the on-eye lens movement which is essential for extended wear of contact lenses. Moreover, the materials obtained by the process of the invention provide additional effects being essential for lenses for extended wear, such as an increased thickness of the pre-lens tear film which contributes substantially to low microbial adhesion and resistance to deposit formation. Due to the extremely soft and lubricious character of the novel surface coatings, biomedical articles such as in particular contact lenses coated by the process of the invention show a superior wearing comfort including improvements with respect to late day dryness and long term (overnight) wear. The novel surface coatings moreover interact in a reversible manner with occular mucus which contributes to the improved wearing comfort.

In addition, biomedical devices, e.g. ophthalmic devices such as contact lenses, coated by the process of the invention, have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the materials obtained according to the invention is excellent. In addition, the attachment of a hydrophilic surface coating at a given bulk material according to the invention does not affect its visual transparency.

In summary, the ophthalmic devices obtained by the process of the invention, such as contact lenses and artificial cornea, provide a combination of low spoilation with respect to cell debris, cosmetics, dust or dirt, solvent vapors or chemicals, with a high comfort for the patient wearing such ophthalmic devices in view of the soft hydrogel surface which for example provides a very good on-eye movement of the ohthalmic device. Biomedical devices such as adhesion barriers in tissue surgery, renal dialysis membranes, blood storage bags, pacemaker leads or cardiovascular devices such as heart valves and artificial blood vessels (vascular grafts) coated by the process of the invention resist fouling by proteins, thus reducing the rate and extent of thrombosis. Blood-contacting devices fabricated according to the present invention are therefore haemocompatible and biocompatible. Diagnostics and biosensing applications suffer from reduced signal-to-noise ratios when non-specific protein adsorption occurs; hence, the present coatings offer scope for devices with greater range of sensitivity.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Kruss GmbH, Hamburg, Germany). Welling force on the solid is measured as the solid is immersed in or withdrawn from a liquid of known surface tension.

The following examples describe, but do not limit, the invention:

EXAMPLE 1

Comparative example: Grafting of Linear Polyacrylamide Chains

Lotrafilcon contact lenses are first coated in a plasma reactor with a thin polymeric interfacial bonding layer, which is deposited from an allylamine plasma (glow discharge) in the glow followed by afterglow mode, using the following conditions for the initial coating step in the plasma glow mode: monomer pressure 0.15 torr, rf Power 20 W, plasma excitation time 20 sec, rf drive frequency 200 KHz. The plasma glow is then extinguished, the allylamine pressure raised to >10 Torr and maintained for 15 minutes (time of exposure to allylamine vapour flowing through the plasma reactor after the plasma excitation has been turned off), following which the allylamine flow is stopped and the plasma reactor vented.

These amine-functionalized contact lenses are removed from the plasma reactor and placed in acetonitrile (1 ml per lens) to which is added isocyanate ethyl methacrylate (IEM) (1 pipette drop per lens). After two hours the lenses are rinsed first in acetonitrile and then in water.

Alternatively, onto the amine-functionalized contact lenses, acrylic acid islattached using 1-ethyl-3-(3-dimethyl aminopropyl)-dicarbodimide (EDC) and N-hydroxysuccinimide (NHS). For each lens 1 ml of reaction solution is required, each ml containing 19.2 mg EDC and 11.5 mg NHS. The EDC is allowed to react for five minutes before the addition of NHS is made. The pH is adjusted to a value of 9 using 1 M NaOH after the addition of NHS. The reaction solution is left overnight before decanting and washing the lenses in excess water. Graft polymerisation of acrylamide onto the functionalized lens surfaces is carried out by adding 1 g acrylamide to 20 ml water containing 15 lenses. The solution is deaereated by purging with pure nitrogen for 10 minutes before the addition of 0.05 g Vaso 50 (2,2'-Azobis-(2-amidinopropane) dihydrochloride). The reaction solution is then heated to 50° C. and kept at this temperature overnight, with continual $N_2$ purging. After decanting, the lenses are agitated in water for several days, with periodic supply of fresh water to remove residual unreacted polyacrylamide.

Surface analysis by X-ray photoelectron spectroscopy (XPS) revealed the presence of a polyacrylamide coating by the elemental composition and its characteristic C 1s spectrum, as verified both by comparison with published polyacrylamide spectra and spectra recorded on the same instrument using bulk polyacrylamide.

EXAMPLE 2

Grafting of Branched Polyacrylamide-containing Coating

Lotrafilcon contact lenses are surface activated as in example 1. In the graft polymerization step, however, 10% acrylic acid (relative to acrylamide) is added before addition of the initiator, leading to the grafting of acrylamide-co-acrylic acid co-polymer chains. XPS analysis showed the successful grafting of the intended co-polymer. The acrylic acid groups are then used to attach branches. After overnight heating and subsequent washing the lenses are placed into dimethyformamide (DMF, 1 ml per lens) and IEM is added (for each lens one pipette drop). After two hours DMF is used to wash off the excess of IEM, followed by a water-wash cycle. Polymerization of acrylamide onto the attached IEM moieties is then done as in example 1 except at 35° C. over two days with $N_2$ purging. The contact lenses are then thoroughly washed using several cycles of renewing the water. Gas chromatography is used to ascertain the absence of residual acrylamide monomer.

EXAMPLE 3

Crosslinked Polyacrylamide-containing Coating

Lotrafilcon contact lenses are allylamine-plasma-coated and treated with IEM as in example 1 and 2, respectively. In the grafting step, however, a mixture of acrylamide and 2% methylolacrylamide is used and the grafting performed at 35° C. Washing of the contact lenses in water is done as in example 2. The presence of an acrylamide-co-methylolacryl-amide grafted co-polymer is verified by XPS analysis. After washing the lenses are treated with HCl at pH 4 to induce crosslinks between the methylolacrylamide segments.

EXAMPLE 4

Branched and Crosslinked Polyacrylamide-containing Coating

Lotrafilcon contact lenses are allylamine-plasma-coated and treated with IEM as in example 1 and 2, respectively. A branched coating is attached in the same way as in example 2, except that to the second acrylamide polymerisation step 2% methylolacrylamide is added, as in example 3. Thus, a coating containing methylolacrylamide segments in the side branches is produced. These segments are crosslinked in the same way as described in example 3 by lowering the pH to 4.

Test Results: Clinical Testing of Coated Contact Lenses.

Coated Lotrafilcon contact lenses are worn by human volunteers in a controlled clinical environment and retrieved after 6 hours of wear by optometrists using gloved hands. The worn lenses are placed in vials with sterile saline, then placed in distilled water, and finally dried for XPS and MALDI (matrix assisted laser desorption ionization) analysis. The XPS and MALDI spectra show that when coating has been performed according to the comparative example 1, some protein adsorption does occur, although the amount is low, in accordance with prior art data. For coating according to the example 2, however, no spectral changes relative to unworn lenses can be observed, indicating that no adsorbed protein at all is detectable within the highly sensitive experimental limits of XPS and MALDI.

What is claimed:

1. A process for coating a material surface, comprising the steps of:
   (a) providing an organic bulk material having functional groups on its surface;
   (b) covalently binding to the surface of the bulk material a layer of a first compound having a first reactive group and an ethylenically unsaturated double bond by reacting the function groups on the surface of the bulk material with the first reactive group of the first compound;
   (c) copolymerizing, on the surface of the bulk material, a first hydrophilic monomer and a monomer comprising a second reactive group to form a coating comprising a plurality of primary polymer chains which are covalently bonded to the surface through the first compound, wherein each primary polymer chain comprises second reactive;
   (d) reacting the second reactive groups of the primary polymer chains with a second compound comprising an ethylenically unsaturated double bond and a third reactive group that is coreactive with the second reactive group, to covalently bind the second compound to the primary polymer chains; and
   (e) graft-polymerizing a second hydrophilic monomer to obtain a branched hydrophilic coating on the surface of the bulk material, wherein the branched hydrophilic coating comprises the plurality of the primary polymer chains and a plurality of secondary chains each of which is covalently attached through the second compound to one of the primary chains.

2. A process according to claim 1, wherein the functional groups on the surface of the bulk material are selected from the group consisting of hydroxy, amino, alkylamino, thiol and carboxy groups, and wherein the first reactive group is selected from the group consisting of isocyanato, azlactone, epoxy, carboxy anhydride, carboxy and hydroxy groups.

3. A process according to claim 1, wherein the first and second compounds are each independently of the other an ethylenically unsaturated compound having from 2 to 18 C-atoms which is substituted by a reactive group selected from the group consisting of ahydroxy, amino, carboxy, carboxylic acid ester, carboxylic acid anhydride, epoxy, lactone, azlactone and isocyanato groups.

4. A process according to claim 3, wherein the first and second compounds independently of each other has a formula of:

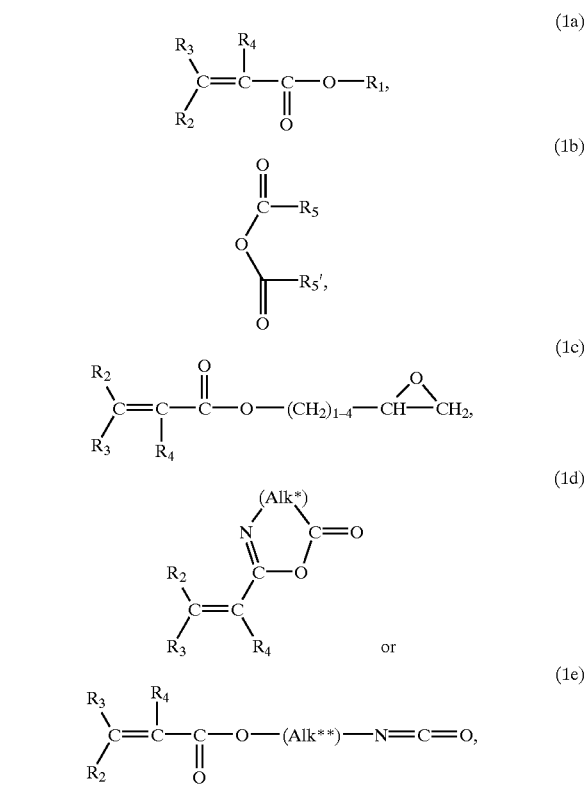

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, carboxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —$C(R_2)$=$C(R_4)$—, and (Alk*) is $C_1$–$C_6$-alkylene, and (Alk**) is $C_2$–$C_{12}$-alkylene.

5. A process according to claim 1, wherein the monomer comprising a second reactive group is a compound having a formula of:

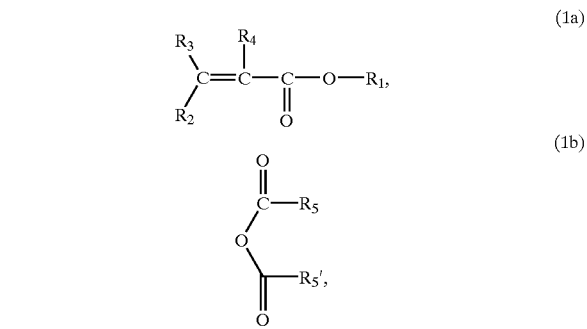

-continued

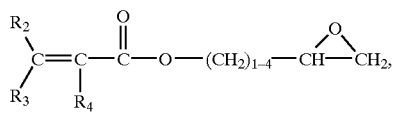
(1c)

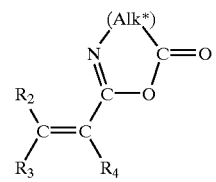
(1d)

or

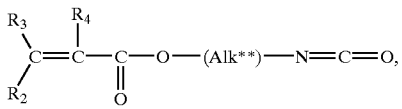
(1e)

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, carboxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —C($R_2$)=C($R_4$)—, and (Alk*) is $C_1$–$C_6$-alkylene, and (Alk**) is $C_2$–$C_{12}$-alkylene; and wherein the first hydrophilic monomer is selected from the group consisting of hydroxy-substituted $C_1$–$C_2$-alkyl acrylates and methacrylates, acrylamide, methacrylamide, N-mono- and N,N-di-$C_1$–$C_2$-alkylacrylamide and -methacrylamide, ethoxylated acrylates and methacrylates, hydroxy-substituted $C_1$–$C_2$-alkyl vinyl ethers, sodium ethylene-sulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino-, mono-$C_1$–$C_2$-alkylamino- and di-$C_1$–$C_2$-alkylamino-$C_1$–$C_2$-alkyl acrylates and methacrylates and allyl alcohol.

6. A process according to claim 1, wherein the second compound has a formula of

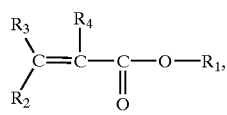
(1a)

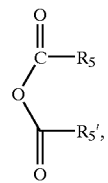
(1b)

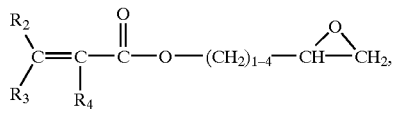
(1c)

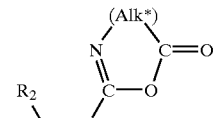
(1d)

or

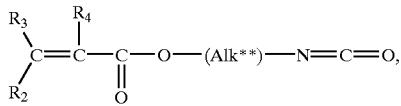
(1e)

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, carboxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —C($R_2$)=C($R_4$)—, and (Alk*) is $C_1$–$C_6$-alkylene, and (Alk**) is $C_2$–$C_{12}$-alkylene; and wherein the second hydrophilic monomer is selected from the group consisting of hydroxy-substituted $C_1$–$C_2$-alkyl acrylates and methacrylates, acrylamide, methacryl-amide, N-mono- and N,N-di-$C_1$–$C_2$-alkylacrylamide and -methacrylamide, ethoxylated acrylates and methacrylates, hydroxy-substituted $C_1$–$C_2$-alkyl vinyl ethers, sodium ethylenesulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino-, mono-$C_1$–$C_2$-alkylamino- and di-$C_1$–$C_2$-alkylamino-$C_1$–$C_2$-alkyl acrylates and methacrylates and allyl alcohol.

7. A process for coating a material surface, comprising the steps of:

(a) providing an organic bulk material having functional groups on its surface;

(b) covalently binding to the surface of the bulk material a layer of a first compound having a first reactive group and an ethylenically unsaturated double bond by reacting the function groups on the surface of the bulk material with the first reactive group of the first compound;

(c) copolymerizing, on the surface of the bulk material, a first hydrophilic monomer and a monomer comprising a second reactive group to form a coating comprising a plurality of primary polymer chains which are covalently bonded to the surface through the first compound, wherein each primary polymer chain comprises second reactive groups;

(d) reacting the second reactive groups of the primary polymer chains with a second compound comprising an ethylenically unsaturated double bond and a third reactive group that is coreactive with the second reactive group, to covalently bind the second compound to the primary polymer chains; and (e) graft-polymerizing a second hydrophilic monomer and a co-monomer having a crosslinkable group to obtain a branched hydrophilic coating on the surface of the bulk material, wherein the branched hydrophilic coating comprises the plurality of the primary polymer chains and a plurality of secondary chains each of which is covalently attached through the second compound to one of the primary chains and comprises crosslinkable groups; and (f) initiating crosslinking of said crosslinkable groups.

8. A process according to claim 7, wherein the functional groups on the surface of the bulk material are selected from the group consisting of hydroxy, amino, alkylamino, thiol and carboxy groups, and wherein the first reactive group is selected from the group consisting of isocyanato, azlactone, epoxy, carboxy anhydride, carboxy and hydroxy groups.

9. A process according to claim 8, wherein the first and second compounds are each independently of the other an ethylenically unsaturated compound having from 2 to 18 C-atoms which is substituted by a reactive group selected from the group consisting of hydroxy, amino, carboxy, carboxylic acid ester, carboxylic acid anhydride, epoxy, lactone, azlactone and isocyanato groups.

10. A process according to claim 9 wherein the first and second compounds independently of each other has a formula of:

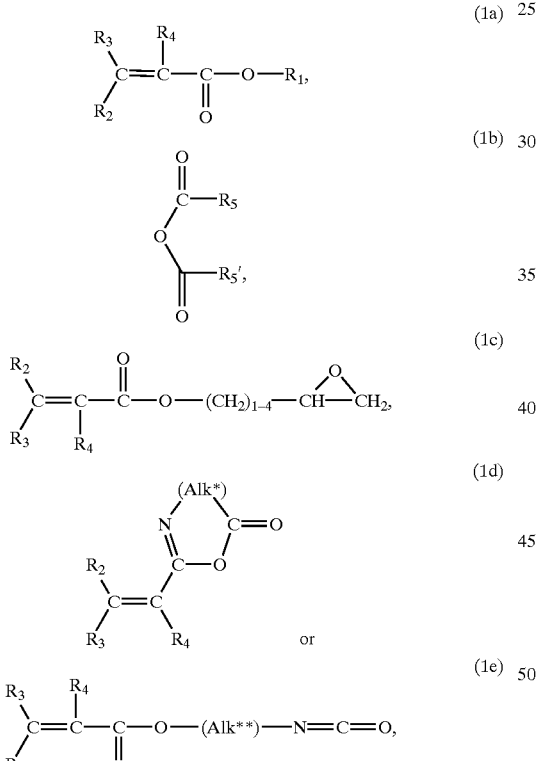

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, car boxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —C($R_2$)=C($R_4$)—, and (Alk*) is $C_1$–$C_6$-alkylene, and (Alk**) is $C_2$–$C_{12}$-alkylene.

11. A process according to claim 7, wherein the monomer comprising a second reactive group is a compound having a formula of:

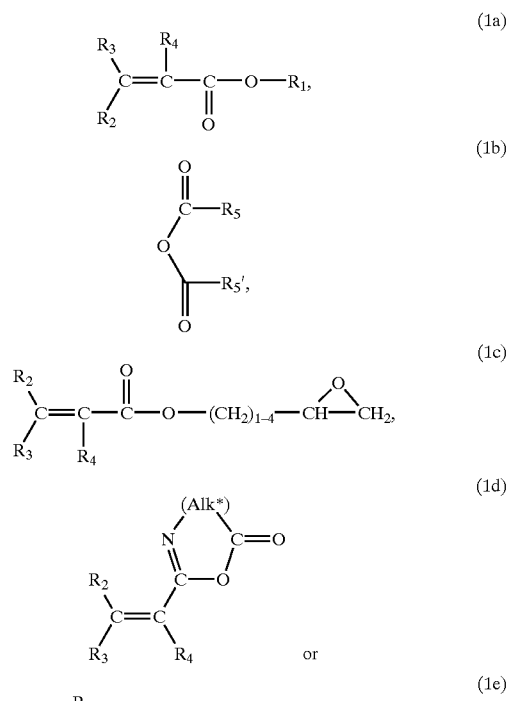

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, carboxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —C($R_2$)=C($R_4$)—, and (Alk*) is $C_1$–$C_6$-alkylene, and (Alk**) is $C_2$–$C_{12}$-alkylene; and wherein the first hydrophilic monomer is selected from the group consisting of hydroxy-substituted $C_1$–$C_2$-alkyl acrylates and methacrylates, acrylamide, methacrylamide, N-mono- and N,N-di-$C_1$–$C_2$-alkylacrylamide and -methacrylamide, ethoxylated acrylates and methacrylates, hydroxy-substituted $C_1$–$C_2$-alkyl vinyl ethers, sodium ethylene-sulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino-, mono-$C_1$–$C_2$-alkylamino- and di-$C_1$–$C_2$-alkylamino-$C_1$–$C_2$-alkyl acrylates and methacrylates and allyl alcohol.

12. A process according to claim 7, wherein the second compound has a formula of

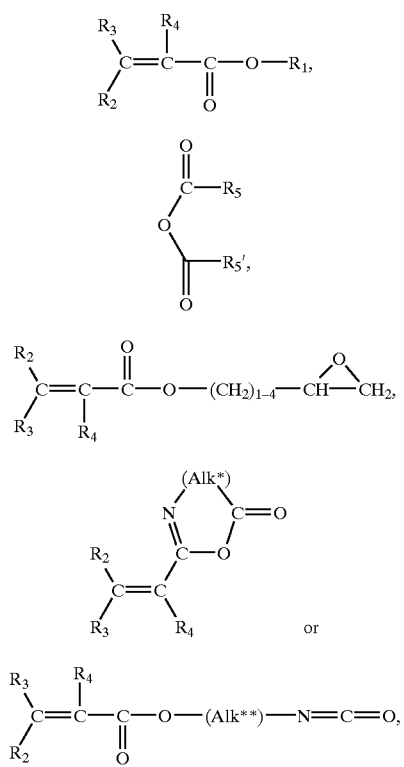

wherein $R_1$ is hydrogen, unsubstituted or hydroxy-substituted $C_1$–$C_6$-alkyl or phenyl, $R_2$ and $R_3$ are each independently of the other hydrogen, $C_1$–$C_4$-alkyl, phenyl, carboxy or halogen, $R_4$ is hydrogen, $C_1$–$C_4$-alkyl or halogen, $R_5$ and $R_5'$ are each an ethylenically unsaturated radical having from 2 to 6 C-atoms, or $R_5$ and $R_5'$ together form a bivalent radical —C($R_2$)=C($R_4$)—, and (Alk*) is $C_1$–$C_6$-alkylene, and (Alk**) is $C_2$–$C_{12}$-alkylene; and wherein the second hydrophilic monomer is selected from the group consisting of hydroxy-substituted $C_1$–$C_2$-alkyl acrylates and methacrylates, acrylamide, methacryl-amide, N-mono- and N,N-di-$C_1$–$C_2$-alkylacrylamide and -methacrylamide, ethoxylated acrylates and methacrylates, hydroxy-substituted $C_1$–$C_2$-alkyl vinyl ethers, sodium ethylenesulfonate, sodium styrenesulfonate, 2-acrylamido-2-methylpropanesulfonic acid, N-vinylpyrrole, N-vinylsuccinimide, five- to seven-membered N-vinyl lactams, 2- or 4-vinylpyridine, amino-, mono-$C_1$–$C_2$-alkylamino- and di-$C_1$–$C_2$-alkylamino-$C_1$–$C_2$-alkyl acrylates and methacrylates and allyl alcohol.

13. A process according to claim 7, wherein the crosslinkable group of the co-monomer is isocyanato, epoxy, hydroxy, amino or carboxy.

* * * * *